(12) United States Patent
Lin et al.

(10) Patent No.: US 11,560,362 B2
(45) Date of Patent: Jan. 24, 2023

(54) DIBUTYLFLUORENE DERIVATIVE AND APPLICATION THEREOF AS PHOTOINITIATOR

(71) Applicant: HUI ZHOU HUAHONG NEW MATERIAL CO., LTD., Huizhou (CN)

(72) Inventors: Jianxiong Lin, Huizhou (CN); Chuanwen Chen, Huizhou (CN)

(73) Assignee: HUIZHOU HUAHONG NEW MATERIAL CO., LTD., Huizhou (CN)

( * ) Notice: Subject to any disclaimer, the term of this patent is extended or adjusted under 35 U.S.C. 154(b) by 182 days.

(21) Appl. No.: 16/765,826

(22) PCT Filed: Nov. 12, 2018

(86) PCT No.: PCT/CN2018/116999
§ 371 (c)(1),
(2) Date: May 20, 2020

(87) PCT Pub. No.: WO2019/101142
PCT Pub. Date: May 31, 2019

(65) Prior Publication Data
US 2020/0385359 A1 Dec. 10, 2020

(30) Foreign Application Priority Data
Nov. 22, 2017 (CN) .......................... 201711175135.1

(51) Int. Cl.
C07D 295/108 (2006.01)
C08F 222/10 (2006.01)
C07C 2/86 (2006.01)
C07C 45/30 (2006.01)
C09D 4/00 (2006.01)
G03F 7/031 (2006.01)

(52) U.S. Cl.
CPC .......... C07D 295/108 (2013.01); C07C 2/861 (2013.01); C07C 45/30 (2013.01); C08F 222/103 (2020.02); C09D 4/00 (2013.01); G03F 7/031 (2013.01)

(58) Field of Classification Search
None
See application file for complete search history.

(56) References Cited

FOREIGN PATENT DOCUMENTS

| CN | 103012317 A | 4/2013 |
|---|---|---|
| CN | 104661997 A | 5/2015 |
| CN | 105916837 A | 8/2016 |
| CN | 106883114 A | 6/2017 |
| CN | 107239003 A | 10/2017 |
| CN | 107272336 A | 10/2017 |
| CN | 107793503 A | 3/2018 |
| CN | 108117616 A | 6/2018 |
| WO | 2019101142 A1 | 5/2019 |

OTHER PUBLICATIONS

International Search Report of PCT/CN2018/116999, (dated Feb. 13, 2019).
Written Opinion of PCT/CN2018/116999, (dated Feb. 2, 2019).

Primary Examiner — Zinna Northington Davis
(74) Attorney, Agent, or Firm — Dragon Sun Law Firm, PC; Jinggao Li; Nathaniel Perkins

(57) ABSTRACT

The present invention provides a dibutylfluorenyl derivative, an application of same as a photoinitiator, and a preparation method therefor. The present invention provides a photo-curing composition including the compound and a photo-curing method using the composition.

20 Claims, No Drawings

DIBUTYLFLUORENE DERIVATIVE AND APPLICATION THEREOF AS PHOTOINITIATOR

TECHNICAL FIELD

The present invention relates to the field of curing by irradiation with emitted light.

Specifically, the present invention provides a novel dibutylfluorenyl derivative, i. e., 2-methyl-1-(2-(9,9-dibutylfluorenyl))-2-(N-morpholinyl)-1-acetone, and a preparation method therefor, and an application of 2-methyl-1-(2-(9,9-dibutylfluorenyl))-2-(N-morpholinyl)-1-acetone as a photoinitiator.

BACKGROUND

Radiation curing technology refers to a new technology that performs irradiation with emitted light such as ultraviolet (UV) light and Electron Beams (EBs), infrared light, visible light, laser light, and chemical fluorescence to cure a polymer, has the characteristics of high efficiency, economy, energy saving, and environmental friendliness, and is a new energy-saving and environmental-protection technology.

Photoinitiators are widely used in domestic coating and ink industries. With improvements of standards of living, people pay more attention to environmental and food safety issues. In the packaging industry, especially color printing in the food and cosmetics packaging industry, there are increasingly strict limits on harmful Volatile Organic Compounds (VOCs) such as benzene, carbon tetrachloride, and chloroform. For example, it is strictly stipulated in the printing of food packages that the maximum limit of a benzene emission is 3 mg/m$^2$, and that of tobacco packaging supplies is 0.01 mg/m$^2$. The relevant standards in American and European countries are stricter. China is a large industrial manufacturing country, and the quantity of products from the packaging industry exported to the American and European countries is increasing. The limit of detection of harmful VOCs in packaging products must satisfy the standards of the American and European countries.

Now commonly used photoinitiators, such as benzophenone and diphenylethanedione, would produce VOCs due to photoinitiation during use, and currently cannot satisfy detection standard requirements in the field of food and cosmetics packaging. Existing certain carbazole and dibenzofuran compound photoinitiators have poor stability during storage and use. In addition, due to high costs of used raw materials, such as carbazole and dibenzofuran, the costs of photoinitiators are high, and there is no special advantage in performance.

The photoinitiators in the prior art also have a disadvantage of low photoinitiation efficiency, in particular, low photoinitiation efficiency in certain wavelength ranges due to a certain limitation on wavelength requirements for an excitation light source.

Therefore, in the technical field of photopolymerization, there is also a need for a photoinitiator is more environmentally friendly, has higher activity, is easy to prepare, and is easy to handle, and a photocuring method.

SUMMARY

The present invention provides a novel compound as a photoinitiator. The present invention further provides a photocuring composition including the novel compound, and provides a curing method using the novel compound and the photocuring composition. The compound, curing composition, and photocuring method provided by the present invention can more effectively initiate photopolymerization in a wavelength range, and the compound provided by the present invention has higher stability, would be easily prepared and handled, and is more environmentally friendly.

Specifically, the present invention provides a photocuring composition, including:

(a) a photoinitiator compound having the following formula:

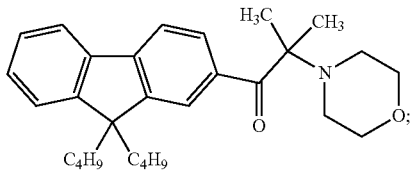

(b) a photopolymerizable carbon-carbon double bond unsaturated compound.

In one aspect of the present invention, the photoinitiator compound in the photocuring composition of the present invention accounts for 0.5-10% by weight of the composition, preferably about 3%.

The photopolymerizable carbon-carbon double bond unsaturated compound in component (b) in the photocuring composition of the present invention includes a compound having one or more olefinic double bonds. Examples of photopolymerizable compound monomers include: alkyl acrylate, alkyl methacrylate, a hydroxyalkyl ester, an epoxy alkyl ester, (meth)acrylamide, N-substituted (meth)acrylamide, an unsaturated carboxylic acid anhydride, an unsaturated ester, a vinyl ether, isocyanurate, an N-vinyl heterocyclic compound, etc.

In one aspect of the present invention, the ethylenically unsaturated photopolymerizable compound is an ester of an ethylenically unsaturated carboxylic acid and a polyol or polyepoxide. Examples of the unsaturated carboxylic acid are acrylic acid, methacrylic acid, and unsaturated fatty acids such as linolenic acid or oleic acid. Preferably, the unsaturated carboxylic acid is acrylic acid and methacrylic acid. The polyol may be an aromatic, aliphatic or cycloaliphatic polyol. Examples of the aromatic polyol are hydroquinone, 4,4-dihydroxybiphenyl, 2,2-bis(4-hydroxyphenyl)propane, and novolac and phenolic resin A. In another aspect of the present invention, the ethylenically unsaturated photopolymerizable compound is an acrylated epoxy resin, alkyl acrylate, alkoxy acrylate, or a mixture thereof, most preferably epoxy acrylate, trimethylolpropane triacrylate, or a mixture thereof.

The ethylenically unsaturated photopolymerizable compound in component (b) may be one of said compounds, or a mixture of two or more of said compounds.

In the photopolymerizable composition of the present invention, the general usage amount of the ethylenically unsaturated photopolymerizable compound in component (b) is about 10% to about 70%, preferably about 25% to about 60%.

The photopolymerizable composition provided by the present invention may further include other additives. For example, a thermal inhibitor that prevents premature polymerization, a light stabilizer (such as an ultraviolet absorbent), etc. Examples of a usable light stabilizer include hydroxyphenylbenzotriazole, hydroxyphenyl-benzophenone, etc.

In still another aspect of the present invention, the photocuring composition of the present invention further includes a reactive amine co-initiator, such as a water-soluble tertiary amine. The amine co-initiator accounts for 0.5-10% by weight of the composition, preferably about 7%.

In still another aspect of the present invention, the photocuring composition of the present invention includes:

| | |
|---|---|
| epoxy acrylate | about 35% |
| reactive amine co-initiator | about 7% |
| trimethylolpropane triacrylate | about 55% |
| photoinitiator | about 3%, | where the percentage is the weight ratio of said component in the composition.

The present invention provides a curing method of the photocuring composition of the present invention, including coating the photocuring composition on a substrate, and performing irradiation with light having a wavelength of 150-600 nm. In one aspect of the present invention, the photocuring composition of the present invention is suitable for curing by irradiation with light in the range of 320-420 nm, preferably 340-400 nm. Examples of a light source or radiation that can be used in the curing method in the aspect of the present invention include a mercury vapor lamp or a laser lamp having an emission band between a UV region and a visible light region.

The present invention provides an application of the photocuring composition of the present invention, where the photocuring composition is used for manufacturing colored and non-colored paints and varnishes, a powder coating, a printing ink, a printing plate, an adhesive, a dental composition, a gel coating, a photoresist for electronics, an electroplating resist, liquid and dry films, a solder resist, a resist for a color filter for display application, a structural resist produced in a manufacturing process for a plasma display panel, an electroluminescent display, and an LCD, an LCD spacer, used for holographic data storage, used as a composition for encapsulating electrical and electronic elements, used for manufacturing a magnetic recording material, a micromechanical component, an optical switch, an electroplating mask, an etching mask, a color proofing system, a glass fiber cable coating, and a screen printing stencil, used for generating a three-dimensional object by means of stereolithography, used as an image recording material, used for holographic recording, used for manufacturing a microelectronic circuit and a decolorizing material, and used for an image recording material using microcapsules.

The present invention further provides a coated substrate, at least one surface of which is coated with the photocuring composition of the present invention.

In one aspect of the present invention, provided is a photoinitiator compound having the formula:

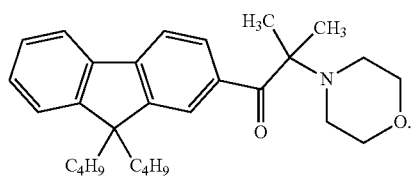

In one aspect of the present invention, provided is a method for preparing a compound of the following formula:

The method includes the following steps:

(1)

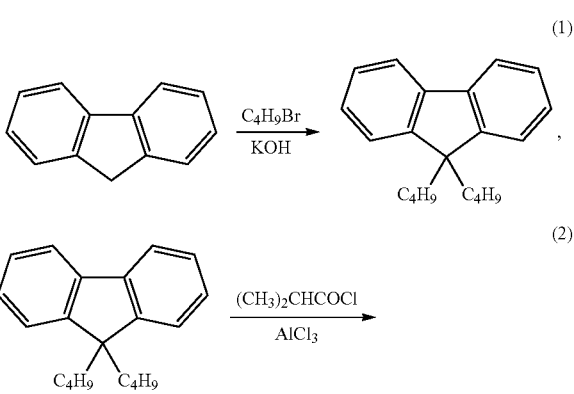

(2)

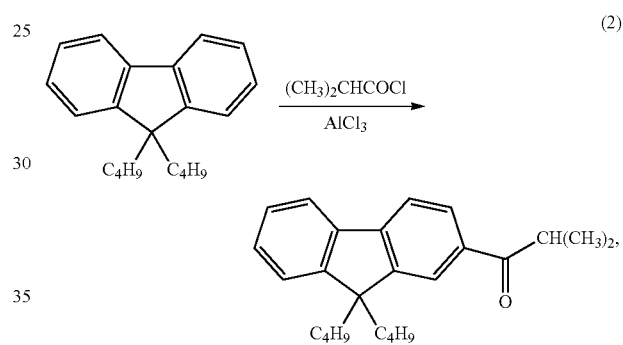

(3)

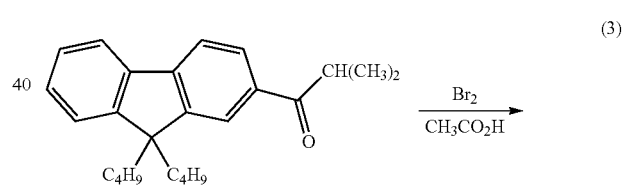

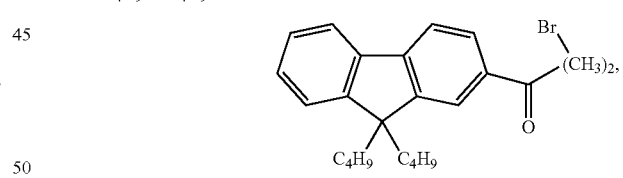

(4)

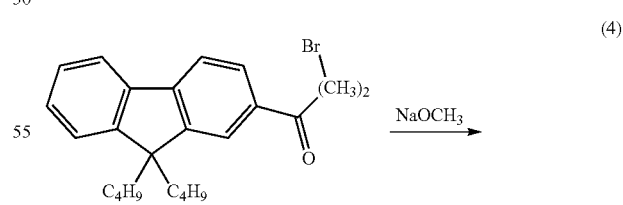

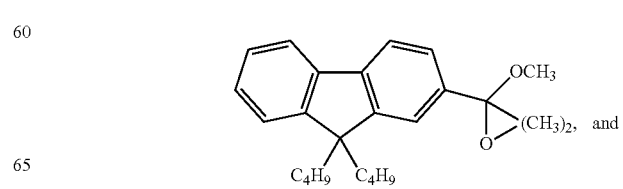

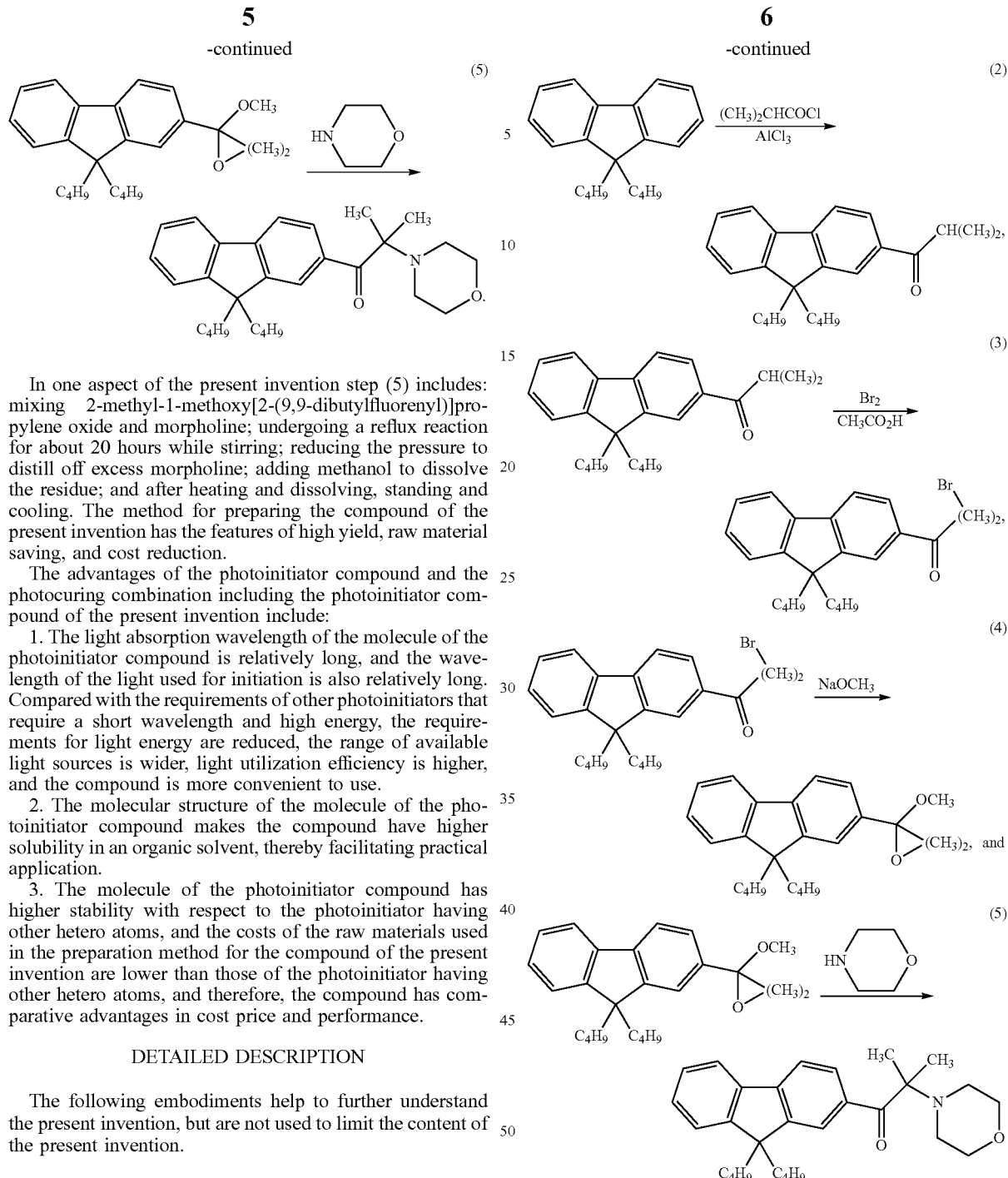

In one aspect of the present invention step (5) includes: mixing 2-methyl-1-methoxy[2-(9,9-dibutylfluorenyl)]propylene oxide and morpholine; undergoing a reflux reaction for about 20 hours while stirring; reducing the pressure to distill off excess morpholine; adding methanol to dissolve the residue; and after heating and dissolving, standing and cooling. The method for preparing the compound of the present invention has the features of high yield, raw material saving, and cost reduction.

The advantages of the photoinitiator compound and the photocuring combination including the photoinitiator compound of the present invention include:

1. The light absorption wavelength of the molecule of the photoinitiator compound is relatively long, and the wavelength of the light used for initiation is also relatively long. Compared with the requirements of other photoinitiators that require a short wavelength and high energy, the requirements for light energy are reduced, the range of available light sources is wider, light utilization efficiency is higher, and the compound is more convenient to use.

2. The molecular structure of the molecule of the photoinitiator compound makes the compound have higher solubility in an organic solvent, thereby facilitating practical application.

3. The molecule of the photoinitiator compound has higher stability with respect to the photoinitiator having other hetero atoms, and the costs of the raw materials used in the preparation method for the compound of the present invention are lower than those of the photoinitiator having other hetero atoms, and therefore, the compound has comparative advantages in cost price and performance.

DETAILED DESCRIPTION

The following embodiments help to further understand the present invention, but are not used to limit the content of the present invention.

Embodiment 1 Synthesis of 2-methyl-1-(2-(9,9-dibutylfluorenyl))-2-(N-morpholinyl)-1-acetone The synthesis route of 2-methyl-1-(2-(9,9-dibutylfluorenyl))-2-(N-morpholinyl)-1-acetone is as follows:

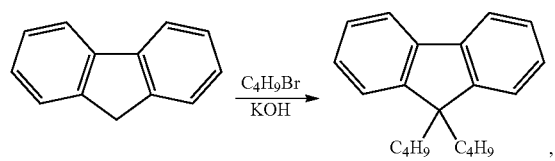

Step (1) Synthesis of 9,9-dibutylfluorene 12 mmol (1.99 g) of fluorene, 0.5 mmol (0.16 g) of phase transfer catalyst tetra-n-butylammonium bromide, 4.5 mL of 50% aqueous sodium hydroxide solution, 29 mmol (3.1 mL) of n-butyl bromide, and 50 mL of butanone are respectively added to a 100 mL three-necked flask. Heating and reflux are performed for 3-4 hours, and the reaction is followed by means of thin-layer chromatography until the reaction is ended. After the solvent butanone is distilled off, extraction is performed with dichloromethane (10 mL×3 times). Organic layers are combined, drying is performed with anhydrous sodium sulfate, and the solvent is removed by rotary evaporation to obtain a target product.

Step (2) Synthesis of 2-(2-methylpropionyl)-9,9-dibutylfluorene 0.01 mol (1.0 mL) of isobutyryl chloride, 0.01 mol (2.78 g) of 9,9-dibutylfluorene, and 40 mL of dichloromethane are respectively added to a 250 mL three-necked flask. Mixing is performed uniformly while magnetically stirring, and cooling is performed in an ice bath. Under magnetic stirring, a total of 0.012 mol (1.58 g) of aluminum trichloride is added in two portions at 10° C. or less, then the temperature is raised to room temperature and stirring is performed for 3 hours, and then the temperature is raised to 40° C. and stirring is continued for 1 hour. The reaction mixture is slowly poured into 100 g of ice water while stirring. After standing and layering, the water layer is separated and removed, and the organic layers are washed with ice water (30 mL×3 times), and is basically neutral. After drying, dichloromethane is removed to obtain a target product.

Step (3) Synthesis of 2-(2-bromo-2-methylpropionyl)-9,9-dibutylfluorene 50 mL of methylene chloride, 15 mL of 80% sulfuric acid, 0.20 mol of hydrogen peroxide, and 0.10 mol (34.85 g) of 2-(2-methylpropionyl)-9,9-dibutylfluorene are added to a 250 mL three-necked flask. The temperature is controlled at 25-30° C., and 0.07 mol (3.6 mL) of bromine is added dropwise within 1.0-1.5 hours. After bromine is added dropwise for 20 minutes, HPLC detects that 2-(2-methylpropionyl)-9,9-dibutylfluorene reacts completely. Under cooling, 30% sodium hydroxide solution is added dropwise while stirring to neutralize the reaction mixture until the pH value is neutral. Standing and layering are performed. The water layer is extracted with dichloromethane (20 mL×2 times). Organic layers are combined, and drying and rotary distillation are performed to remove the solvent methylene chloride to obtain a target product.

Step (4) Synthesis of 2-methyl-1-methoxy[2-(9,9-dibutylfluorenyl)]propylene oxide 50 mL of anhydrous methanol and 0.12 mol (2.76 g) of sodium metal are added to a 250 mL three-necked flask to prepare a methanol solution of sodium methoxide. The temperature is controlled at 25-30° C., and 0.10 mol (4.27 g) of 2-(2-bromo-2-methylpropionyl)-9,9-dibutylfluorene is added in three batches within 1.5-2.0 hours. After the addition is ended, the reaction is continued for 1 hour. After HPLC detects that 2-(2-bromo-2-methylpropionyl)-9,9-dibutylfluorene reacts completely, rotary distillation is performed at 60° C. to remove the solvent methanol and cooling is performed to obtain a white solid. The product is not purified and directly undergoes further reaction.

Step (5) Synthesis of 2-methyl-1-(2-(9,9-dibutylfluorenyl))-2-(N-morpholinyl)-1-acetone Method 1: 3.67 g (10.0 mmol) of the product 2-methyl-1-methoxy[2-(9,9-dibutylfluorenyl)]propylene oxide of the reaction in step (4) is added to a 100 mL reaction flask, 2.61 g (30.0 mmol) of morpholine is added, reaction is undergone for 20 hours while stirring at 120-130° C. After the tracking of the reaction by means of thin-layer chromatography is ended, the pressure is reduced to distill off excess solvents such as morpholine, and then separation and purification are performed by means of column chromatography by using petroleum ether-ethyl acetate as a mobile phase to obtain 3.63 g of the target compound 2-methyl-1-(2-(9,9-dibutylfluorenyl))-2-(N-morpholinyl)-1-acetone, with the yield being 83.7%. 1H NMR (400 MHz, CDCl$_3$) δ: 8.74 (d, J=0.8 Hz, 1H), 8.48 (dd, J1=8.0 Hz, J2=0.8 Hz, 1H), 7.78-7.73 (m, 2H), 7.39-7.37 (m, 3H), 3.74 (t, J=4.8 Hz, 4H), 2.66-2.64 (m, 4H), 2.05-2.00 (m, 4H), 1.59 (s, 6H), 1.13-1.06 (m, 4H), 0.69-0.60 (m, 10H); 13C NMR (100 MHz, CDCl3) δ: 202.9, 151.9, 149.8, 145.2, 140.0, 129.6, 128.1, 127.0, 125.0, 123.0, 120.6, 119.0, 76.9, 67.4, 55.0, 47.1, 40.1, 26.0, 23.0, 20.4, 13.8. ESRMs m/z=434.3 [M+H]+.

According to nuclear magnetic resonance spectrum (hydrogen spectrum and carbon spectrum) and mass spectrometry results, the product is determined as the target product, 2-methyl-1-(2-(9,9-dibutylfluorenyl))-2-(N-morpholinyl)-1-acetone.

Method 2: 7.33 g (20.0 mmol) of the product 2-methyl-1-methoxy[2-(9,9-dibutylfluorenyl)]propylene oxide of the reaction in step (4) is added to a 100 mL reaction flask, 4.35 g (50.0 mmol) of morpholine is added, and reflux reaction is undergone for 20 hours while stirring. After the tracking of the reaction by means of thin-layer chromatography is ended, the pressure is reduced to distill off the excess morpholine, methanol is added to dissolve the residue, heating is performed to completely dissolve the residue, and standing and cooling are performed to obtain 7.14 g of the target product, 2-methyl-1-(2-(9,9-dibutylfluorenyl))-2-(N-morpholinyl)-1-acetone, with the yield being 82.3%.

Nuclear magnetic resonance spectrum (hydrogen spectrum and carbon spectrum) and mass spectrometry results are the same as those in Synthesis Method 1, i. e., the product is the target product, 2-methyl-1-(2-(9,9-dibutylfluorenyl))-2-(N-morpholinyl)-1-acetone.

Method 3: 7.33 g (20.0 mmol) of the product 2-methyl-1-methoxy[2-(9,9-dibutylfluorenyl)]propylene oxide of the reaction in step (4) is added to a 100 mL reaction flask, 1.74 g (20.0 mmol) of morpholine and 10 mL of N,N-dimethylformamide are added, and reflux reaction is undergone for 20 hours while stirring.

Post-treatment is the same as that in Synthesis Method 2.5.04 g of the target product, 2-methyl-1-(2-(9,9-dibutylfluorenyl))-2-(N-morpholinyl)-1-acetone is obtained, with the yield being 58.1%.

Method 4: 7.33 g (20.0 mmol) of the product 2-methyl-1-methoxy[2-(9,9-dibutylfluorenyl)]propylene oxide of the reaction in step (4) is added to 100 mL reaction flask, 1.74 g (100.0 mmol) of morpholine is added, and a reflex reaction is undergone for 20 hours while stirring. Post-treatment is the same as that in Synthesis Method 2.7.32 g of the target product, 2-methyl-1-(2-(9,9-dibutylfluorenyl))-2-(N-morpholinyl)-1-acetone is obtained, with the yield being 84.4%.

The product yield (83.7%) of Method 1 is slightly higher than the product yield (82.3%) of Method 2. In Method 2, it is not required to separate and purify the product by means of column chromatography, and Method 2 is more suitable for industrial production.

In Method 3, when the molar ratio of the reaction raw material, 2-methyl-1-methoxy[2-(9,9-dibutylfluorenyl)]propylene oxide to the reaction raw material, morpholine, is 1:1, and the yield is low and is only 58.1%; and because 2-methyl-1-methoxy[2-(9,9-dibutylfluorenyl)]propylene oxide is solid at room temperature, the two reaction raw materials are slightly inadequate to dissolve each other.

In Method 4, when the molar ratio of the reaction raw material, 2-methyl-1-methoxy[2-(9,9-dibutylfluorenyl)]propylene oxide to the eaction raw material, morpholine, is 1:5, the product yield (84.4%) does not increase significantly compared with the yield (82.3%) of Synthesis Method 2. However, the amount of morpholine at the molar ratio is increased from 2.5 to 5.0, and the amount of morpholine is increased significantly.

Embodiment 2 Preparation of Photocuring Varnish Formulation

The photocuring varnish formulation is configured according to the following formulation.
The specific formulation is as follows:

| Components | % by weight of the total weight of the composition |
|---|---|
| epoxy acrylate | 35% |
| Active amine P115 | 7% |
| trimethylolpropane triacrylate | 55% |
| Photoinitiator | 3% |

According to the formulation, 2-methyl-1-(2-(9,9-dibutylfluorenyl))-2-(N-morpholinyl)-1-acetone is used as a photoinitiator to prepare the invention formulation.

Comparative formulations prepared by other photoinitiators are prepared and tested by preparing photocuring varnish formulations having only different photoinitiator contents and other formulations with the same composition.

The comparative formulations include:
Comparative formulation 1 prepared by using 2-methyl-1-[4-methylthiophenyl]-2-morpholinyl-1-acetone as a photoinitiator; and
Comparative formulation 2 prepared by using 2-methyl-1-(4-biphenyl)-2-morpholinyl-1-acetone as a photoinitiator.

Embodiment 3 Curing Effect Test

The varnish formulation prepared in Embodiment 2 is coated on blank paper with a thickness of about 15 microns by using a printability tester, an ultraviolet lamp with an adjustable filter with the power of 50 W/CM line power is used in the wavelength range of 360-420 to perform curing at a speed of 100 m/min, and the number of passes under the lamp required to obtain a good surface and perform complete curing is recorded. The results are shown in Table 1 below.

TABLE 1

Results of measurement of the effect of curing by irradiation with UV

| Varnish formulation | Photoinitiator | Number of passes required for complete curing |
|---|---|---|
| Invention formulation | 2-methyl-1-(2-(9,9-dibutylfluorenyl))-2-(N-morpholinyl)-1-acetone | 2 |
| Comparative formulation 2 | 2-methyl-1-(4-biphenyl)-2-morpholinyl-1-acetone | 4 |

Embodiment 4 VOC Emission Analysis

The emissions of VOCs in the cured film prepared with the photoinitiator of the present invention in Embodiment 3 are measured by using headspace gas chromatography.

The results are shown in Table 2 below.

TABLE 2

Results of measurement of emissions of harmful VOCs in the cured layer of a coating by means of headspace gas chromatography

| Serial number | VOC | Measured value (Unit: PPm) | Index value (Unit: PPm) |
|---|---|---|---|
| 1 | Ethanol | 543.4 | / |
| 2 | Acetone | 1.3 | 200 |
| 3 | Isopropyl alcohol | 5.6 | 200 |
| 4 | Butanone | 0.2 | 100 |
| 5 | Ethyl acetate | 5.7 | / |
| 6 | Benzene | / | 4 |
| 7 | Isopropyl acetate | 0.3 | / |
| 8 | Propylene glycol monomethyl ether | / | 500 |
| 9 | N-butyl alcohol | / | 100 |
| 10 | N-propyl acetate | 12.3 | / |
| 11 | 4-methyl-2-pentanone | / | 200 |
| 12 | Methylbenzene | 0.2 | 100 |
| 13 | N-butyl acetate | 1.5 | 100 |
| 14 | Ethylbenzene | 0.8 | 50 |
| 15 | Dimethylbenzene | 3.3 | 50 |
| 16 | Cyclohexanone | 1 | 50 |

Embodiment 5 Solubility, Yellowing and Odor Analysis

A solid photoinitiator (the compound, 2-methyl-1-(2-(9,9-dibutylfluorenyl))-2-(N-morpholinyl)-1-acetone, of the present invention, and a comparative photoinitiator, 2-methyl-1-[4-methylthiophenyl]-2-morpholinyl-1-propanone and 2-methyl-1-(4-biphenyl)-2-morpholinyl-1-acetone

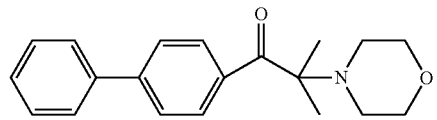 [SMILES: CC(C)(C(=O)c1ccc(-c2ccccc2)cc1)N1CCOCC1]

are dissolved in a liquid polymerized monomer, (1,6-hexanediol diacrylate (HDDA) or tripropylene glycol diacrylate (TPGDA)), heating is performed to 50-60° C. and mixing is performed uniformly. The liquid obtained after dissolving should be stored at room temperature. The solubility of the compound is measured. The degree of yellowing is observed and the odor is manually evaluated. The results are shown in Table 3 below.

TABLE 3

Results of analysis and measurement of solubility, yellowing and odor

| | Initiator compound | 2-methyl-1-[4-methylthiophenyl]-2-morpholinyl-1-acetone | 2-methyl-1-(4-biphenyl)-2-morpholinyl-1-acetone | 2-methyl-1-(2-(9,9-dibutylfluorenyl))-2-(N-morpholinyl)-1-acetone (the present patent compound) |
|---|---|---|---|---|
| Solubility, % (mass fraction) | Polymerized monomer 1: HDDA | 35 | 20 | 50 |
| | Polymerized monomer 2: TPGDA | 22 | 15 | 40 |
| Yellowing after curing | | Yellowing | No yellowing | No yellowing |
| Odor after curing | | Stench | No odor | No odor |

Embodiment 6 Stability Analysis

The varnish formulation prepared in Embodiment 2 is applied to 12×12 cm paperboard with a 15-micron wire rod applicator, and cured with a medium-pressure mercury arc lamp with the power of 80 W/cm at a speed of 20 m/min. The cardboard is cut to a size of 10×10 cm, is completely immersed in two analog solutions, i. e., 100 ml distilled water and 3% acetic acid aqueous solution, sealing is performed well, and placement is performed at 40° C. for 10 days. The printed matter is taken out, and after standing, the contents of the initiator compounds in the analog solutions are directly analyzed by means of HPLC. Calculation is performed by packaging 1 kg of food in a printing area of 600 cm$^2$, the measurement result of mobility is expressed in g/Kg of food, and the results are shown in Table 4.

TABLE 4

Stability analysis results

| | Initiator compound | Mobility ug/kg | |
|---|---|---|---|
| | | Water | 3% acetic acid |
| Comparative formulation 1 | 2-methyl-1-[4-methylthiophenyl]-2-morpholinyl-1-acetone | 1000 | 4000 |
| Comparative formulation 2 | 2-methyl-1-(4-biphenyl)-2-morpholinyl-1-acetone | 80 | 98 |
| Invention formulation | 2-methyl-1-(2-(9,9-dibutylfluorenyl))-2-(N-morpholinyl)-1-acetone | 50 | 60 |

The present inventor has surprisingly found that the innovative compound, 2-methyl-1-(2-(9,9-dibutylfluorenyl))-2-(N-morpholinyl)-1-acetone, has good performance in photopolymerization and can effectively produce polymerization initiation groups when irradiated with UV light, for example. Moreover, the production costs of the photoinitiator compound and the curing composition provided by the present invention are low, the production processes are simple, post-treatment is simple, and the requirements for environmental protection are satisfied. The photoinitiator provided by the present invention can effectively reduce the release of various VOCs, including benzene or toluene, in products and is suitable for packaging and printing industries such as food, tobacco, and cosmetics.

What is claimed is:

1. A photocuring composition, comprising:
   (a) a photoinitiator compound having the following formula:

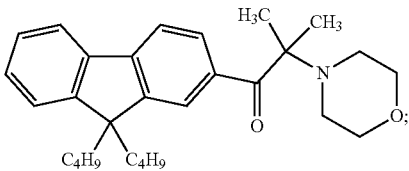

and
   (b) a photopolymerizable carbon-carbon double bond unsaturated compound.

2. The photocuring composition according to claim 1, wherein the photoinitiator compound accounts for 0.5-10% by weight of the composition.

3. The photocuring composition according to claim 1, wherein the carbon-carbon double bond unsaturated compound is an ester of ethylenically unsaturated carboxylic acid and a polyol or an ester of ethylenically unsaturated carboxylic acid and polyepoxide.

4. The photocuring composition according to claim 1, further comprising a reactive amine co-initiator wherein the amine co-initiator accounts for 0.5-10% by weight of the composition.

5. The photocuring composition according to claim 1, comprising:

| epoxy acrylate | about 35% |
| reactive amine co-initiator | about 7% |
| trimethylolpropane triacrylate | about 55% and |
| photoinitiator | about 3%, | wherein the percentage is the weight ratio of said component in the composition.

6. The photocuring composition according to claim 1, wherein the photocuring composition is used for manufacturing colored and non-colored paints and varnishes, a powder coating, a printing ink, a printing plate, an adhesive, a dental composition, a gel coating, a photoresist for electronics, an electroplating resist, liquid and dry films, a solder resist, a resist for a color filter for display application, a structural resist produced in a manufacturing process for a plasma display panel, an electroluminescent display, and an LCD, an LCD spacer, used for holographic data storage, used as a composition for encapsulating electrical and electronic elements, used for manufacturing a magnetic recording material, a micromechanical component, an optical switch, an electroplating mask, an etching mask, a color proofing system, a glass fiber cable coating, and a screen printing stencil, used for generating a three-dimensional object by means of stereolithography, used as an image recording material, used for holographic recording, used for manufacturing a microelectronic circuit and a decolorizing material, and used for an image recording material using microcapsules.

7. The photocuring composition according to claim 1, comprising coating the photocuring composition on a substrate, and performing irradiation with light having a wavelength of 150-600 nm.

8. A photoinitiator compound having the following formula:

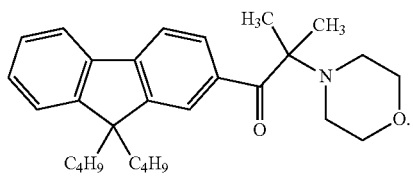

9. A method for preparing the compound of the following formula:

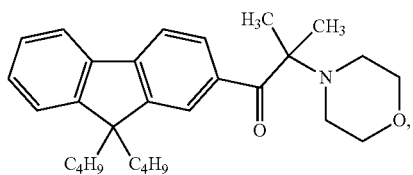

comprising the following steps:

(1)
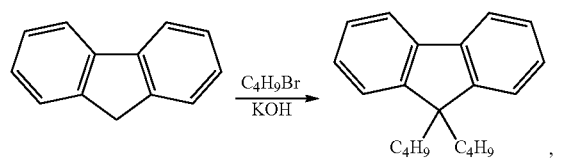

(2)
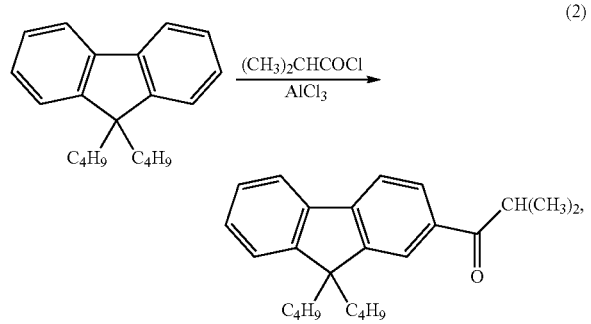

(3)
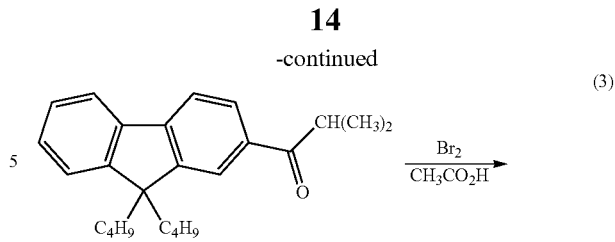

(4)
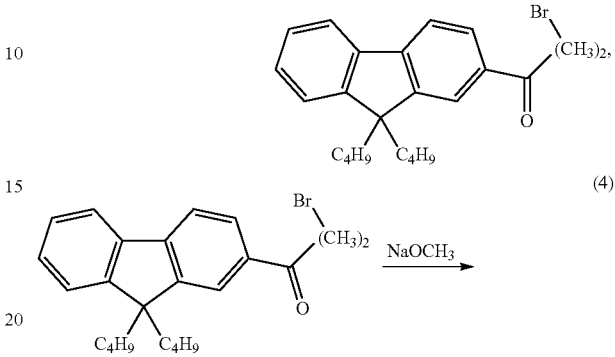

(5)
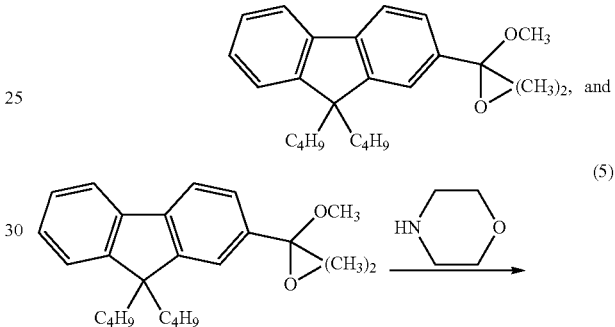

10. The method according to claim 9, wherein step (5) comprises: mixing 2-methyl-1-methoxy[2-(9,9-dibutylfluorenyl)]propylene oxide and morpholine; undergoing a reflux reaction for about 20 hours while stirring; reducing the pressure to distill off excess morpholine; adding methanol to dissolve the residue; and after heating and dissolving, standing and cooling.

11. The photocuring composition according to claim 2, further comprising a reactive amine co-initiator wherein the amine co-initiator accounts for 0.5-10% by weight of the composition.

12. The photocuring composition according to claim 3, further comprising a reactive amine co-initiator wherein the amine co-initiator accounts for 0.5-10% by weight of the composition.

13. The photocuring composition according to claim 2, wherein the photocuring composition is used for manufacturing colored and non-colored paints and varnishes, a powder coating, a printing ink, a printing plate, an adhesive, a dental composition, a gel coating, a photoresist for electronics, an electroplating resist, liquid and dry films, a solder resist, a resist for a color filter for display application, a structural resist produced in a manufacturing process for a plasma display panel, an electroluminescent display, and an LCD, an LCD spacer, used for holographic data storage, used as a composition for encapsulating electrical and electronic elements, used for manufacturing a magnetic recording material, a micromechanical component, an optical switch, an electroplating mask, an etching mask, a color proofing system, a glass fiber cable coating, and a screen printing stencil, used for generating a three-dimensional object by means of stereolithography, used as an image recording material, used for holographic recording, used for manufacturing a microelectronic circuit and a decolorizing material, and used for an image recording material using microcapsules.

14. The photocuring composition according to claim 13, wherein the photoinitiator compound accounts for 0.5-10% by weight of the composition.

15. The photocuring composition according to claim 13, wherein the carbon-carbon double bond unsaturated compound is an ester of ethylenically unsaturated carboxylic acid and a polyol or an ester of ethylenically unsaturated carboxylic acid and polyepoxide.

16. The photocuring composition according to claim 13, further comprising a reactive amine co-initiator wherein the amine co-initiator accounts for 0.5-10% by weight of the composition.

17. The photocuring composition according to claim 13, comprising:

| | |
|---|---|
| epoxy acrylate | about 35% |
| reactive amine co-initiator | about 7% |
| trimethylolpropane triacrylate | about 55% and |
| photoinitiator | about 3%, | wherein the percentage is the weight ratio of said component in the composition.

18. The photocuring composition according to claim 2, comprising coating the photocuring composition on a substrate, and performing irradiation with light having a wavelength of 150-600 nm.

19. The photocuring composition according to claim 2, wherein the photoinitiator compound accounts for 3% by weight of the composition.

20. The photocuring composition according to claim 4, wherein the reactive amine co-initiator comprises a water-soluble tertiary amine, and the amine co-initiator accounts for 7% by weight of the composition.

\* \* \* \* \*